(12) United States Patent
Vardy

(10) Patent No.: US 11,058,919 B2
(45) Date of Patent: *Jul. 13, 2021

(54) SYSTEM AND METHOD FOR FACILITATING PATIENT REHABILITATION

(71) Applicant: IsoTechnology Pty Ltd, Burleigh Waters (AU)

(72) Inventor: Terence Vardy, Tweed Heads (AU)

(73) Assignee: IsoTechnology Pty Ltd, Burleigh Waters (AU)

( * ) Notice: Subject to any disclaimer, the term of this patent is extended or adjusted under 35 U.S.C. 154(b) by 30 days.

This patent is subject to a terminal disclaimer.

(21) Appl. No.: 16/553,607

(22) Filed: Aug. 28, 2019

(65) Prior Publication Data

US 2020/0047032 A1 Feb. 13, 2020

Related U.S. Application Data

(63) Continuation of application No. 14/292,455, filed on May 30, 2014, now Pat. No. 10,398,938.

(51) Int. Cl.
| | |
|---|---|
| *A63B 26/00* | (2006.01) |
| *A61B 5/103* | (2006.01) |
| *G03H 1/00* | (2006.01) |
| *A61B 5/00* | (2006.01) |
| *A63B 71/00* | (2006.01) |

(52) U.S. Cl.
CPC .......... *A63B 26/003* (2013.01); *A61B 5/1036* (2013.01); *A61B 5/4023* (2013.01); *A61B 5/4848* (2013.01); *A61B 5/706* (2013.01); *A61B 5/7435* (2013.01); *A61B 5/7445* (2013.01);

(Continued)

(58) Field of Classification Search
CPC ... A63B 26/003; A63B 5/1036; A63B 5/4023; A63B 5/4848; A63B 5/706; A63B 5/7435; A63B 5/7445; A63B 71/0054; A63B 2214/00; A63B 5/4836; G03H 1/0005
See application file for complete search history.

(56) References Cited

U.S. PATENT DOCUMENTS 4,885,687 A * 12/1989 Carey .................... A61B 5/225
434/261
5,654,810 A * 8/1997 Okamura ............. G02B 3/0056
349/112

(Continued)

FOREIGN PATENT DOCUMENTS

WO WO 2006100675 A2 9/2006

OTHER PUBLICATIONS

SSX Tricky, 2001, https://www.youtube.com/watch?v=5SfhqvmtsYM.

(Continued)

*Primary Examiner* — Garrett K Atkinson
(74) *Attorney, Agent, or Firm* — Bradley Arant Boult Cummings LLP

(57) ABSTRACT

A system and method for rehabilitating a patient. In some embodiments, a patient or other subject can stand on a balance plate and perform one or more tests in response to instructions or visual stimuli on a display screen. Data, such as Centre of Pressure data, can be obtained from the balance plate and processed by a processor in tandem with the progression of a test presented on the display screen. The information can be correlated and used to assist in diagnosing or rehabilitating the patient or subject.

20 Claims, 19 Drawing Sheets

(52) U.S. Cl.
CPC ....... *A63B 71/0054* (2013.01); *G03H 1/0005* (2013.01)

(56) References Cited

U.S. PATENT DOCUMENTS

| | | | | |
|---|---|---|---|---|
| 5,785,632 | A | 7/1998 | Greenberg et al. ............... | 482/5 |
| 5,919,149 | A * | 7/1999 | Allum .................. | A61B 5/1116 |
| | | | | 600/595 |
| 5,987,982 | A | 11/1999 | Wenman et al. .......... | 73/379.08 |
| 6,389,883 | B1 | 5/2002 | Berme et al. ................ | 73/65.01 |
| 6,537,076 | B2 * | 3/2003 | McNitt ............. | A63B 24/0003 |
| | | | | 434/247 |
| 6,616,613 | B1 | 9/2003 | Goodman ..................... | 600/504 |
| 6,641,533 | B2 | 11/2003 | Causey, III et al. .......... | 600/300 |
| 6,684,276 | B2 | 1/2004 | Walker et al. .................. | 710/73 |
| 7,515,044 | B2 | 4/2009 | Welch et al. ............ | 340/539.12 |
| 7,860,725 | B2 * | 12/2010 | Gopinathan ........... | A61B 5/411 |
| | | | | 705/2 |
| 8,007,450 | B2 | 8/2011 | Williams ...................... | 600/595 |
| 8,100,700 | B2 | 1/2012 | Yamazaki ...................... | 463/39 |
| 8,100,770 | B2 * | 1/2012 | Yamazaki ............... | A63F 13/06 |
| | | | | 463/39 |
| 8,255,238 | B2 * | 8/2012 | Powell .................. | G01D 21/00 |
| | | | | 705/3 |
| 8,398,546 | B2 | 3/2013 | Pacione et al. ............... | 600/300 |
| 8,503,086 | B2 * | 8/2013 | French .................... | A63F 13/10 |
| | | | | 359/630 |
| 8,979,722 | B2 * | 3/2015 | Klein .................... | A63F 13/245 |
| | | | | 482/146 |
| 9,202,386 | B2 * | 12/2015 | Yuasa .................. | A61B 5/1036 |
| 10,251,608 | B2 * | 4/2019 | Galasso ............... | A61B 5/4561 |
| 2002/0127529 | A1 * | 9/2002 | Cassuto ................... | G09B 5/02 |
| | | | | 434/335 |
| 2005/0021370 | A1 | 1/2005 | Riff et al. .......................... | 705/2 |
| 2005/0159674 | A1 | 7/2005 | Harbin et al. ................ | 600/558 |
| 2007/0196800 | A1 * | 8/2007 | Douthit .............. | A63B 69/3667 |
| | | | | 434/252 |
| 2008/0261696 | A1 * | 10/2008 | Yamazaki ............... | A63F 13/06 |
| | | | | 463/39 |
| 2011/0034784 | A1 | 2/2011 | David et al. .................. | 600/301 |
| 2011/0256983 | A1 * | 10/2011 | Malack ............... | A63B 23/0405 |
| | | | | 482/4 |
| 2012/0264579 | A1 * | 10/2012 | Klein ..................... | A63B 22/18 |
| | | | | 482/146 |
| 2013/0171600 | A1 * | 7/2013 | Yuasa .................... | G09B 19/00 |
| | | | | 434/258 |
| 2014/0081177 | A1 * | 3/2014 | Eguibar ............... | A61B 5/1036 |
| | | | | 600/595 |
| 2015/0246260 | A1 * | 9/2015 | Giannelli ......... | A63B 21/00069 |
| | | | | 482/8 |
| 2015/0328497 | A1 * | 11/2015 | Doucot ............ | A63B 21/00181 |
| | | | | 482/146 |

OTHER PUBLICATIONS

SSX Tricky, EA Sports Big. 2001. (Year: 2001).
International Search Report and Written Opinion, dated Apr. 8, 2014, in Application PCT/US2014/000149.
European Search Report dated Feb. 13, 2018 of corresponding European Patent Application No. 15799094.6.
Non-Final Office Action dated Jan. 15, 2016 of corresponding U.S. Appl. No. 14/292,455.
Final Office Action dated Sep. 22, 2016 of corresponding U.S. Appl. No. 14/292,455.
Non-Final Office Action dated Jun. 2, 2017 of corresponding U.S. Appl. No. 14/292,455.
Final Office Action dated Jan. 17, 2018 of corresponding U.S. Appl. No. 14/292,455.
Advisory Action dated Jun. 4, 2018 of corresponding U.S. Appl. No. 14/292,455.
Non-Final Office Action dated Jul. 13, 2018 of corresponding U.S. Appl. No. 14/292,455.
Final Office Action dated Feb. 4, 2019 of corresponding U.S. Appl. No. 14/292,455.

* cited by examiner

SYSTEM AND METHOD FOR FACILITATING PATIENT REHABILITATION

FIELD OF THE INVENTION

The present invention relates generally to devices designed to diagnose human disorders and evaluate rehabilitation.

BACKGROUND

Posturography is a general term that covers all the techniques used to quantify postural control in an upright stance position—either static or dynamic. Among them, Computerized Dynamic Posturography (CDP), also called Test of Balance (TOB), is a non-invasive specialized clinical assessment technique used to quantify the central nervous system adaptive mechanisms (sensory, motor and central) involved in the control of posture and Balance; both in normal (such as in physical education and sports training) and abnormal conditions (particularly in the diagnosis of balance disorders and physical therapy treatment and postural re-education).

Due to the complex interactions among sensory, motor, and central processes involved in posture and balance, CDP requires different protocols in order to differentiate among the many defects and impairments which may affect the patient's postural control system. Thus, CDP is challenged by using several combinations of visual and support surface stimuli and parameters.

Center of gravity (COG) is an important component of balance and should be assessed when evaluating an individual's posture. COG is often measured with Center of Pressure (COP) because COG is hard to quantify.

According to academic literature, the COG should be located at the midpoint of the base of support if an individual has ideal posture. COP excursion and velocity are indicators of control over COG and are key factors for identifying proper posture and the ability of the individual to maintain balance. COP excursion has been defined in the field as the Euclidean displacement in the anterior/posterior and medial/lateral directions within the base of support (perimeter around the feet). With poor posture and/or exaggerated spinal curvatures it is possible that the COP excursion would increase, which can in turn cause instability as the COP shifts towards the periphery of the base of support.

There are various options for treating balance disorders. One option includes treatment for a disease or disorder that may be contributing to the balance problem, for example, ear infection, stroke, multiple sclerosis, spinal cord injury, Parkinson's Disease, neuromuscular conditions, acquired brain injury, cerebellar dysfunction and/or ataxia. Individual treatment will vary and will be based upon assessment results including symptoms, medical history, general health, and the results of the assessment tests.

Many types of balance disorders will require balance training or rehabilitation, prescribed by a medical practitioner, osteopath, chiropractor, occupational therapist or physiotherapist. Osteopaths, chiropractors and physiotherapists often administer standardized outcome measures as part of their assessment in order to gain useful information and data about a patient's current health status and progress.

Rehabilitation for loss of vestibular function must be customized for each patient as studies show that individuals vary in their sensory dependence and how they compensate for vestibular loss. Control of postural orientation and equilibrium can be significantly improved in patients with bilateral or unilateral vestibular loss as long as it is considered a complex, sensory motor skill that must be learned with appropriate feedback and active, context-specific training.

It will be clearly understood that, if a prior art publication is referred to herein, this reference does not constitute an admission that the publication forms part of the common general knowledge in the art in any country.

SUMMARY

Disclosed herein is a system for patient rehabilitation. The system can include a balance plate for measuring Center of Pressure (COP) dynamic weight distribution data of the patient, the balance plate including at least one load cell. The system can further include a visual display, and a processor in operative communication with the balance plate. The processor can be configured to generate data pertaining to the ability of the patient to control their COP by means of body movement, with both their feet in continuous maximal contact with the balance plate surface, from a first predetermined point to at least a second predetermined point as displayed on the Visual display, the data being generated using the COP dynamic weight distribution data as measured by the balance plate.

Also disclosed is a method for evaluating a patient's rehabilitation. The method can include showing, on a display, a first predetermined point and at least a second predetermined point; measuring, with a balance plate, the patient's center of pressure; representing the patient's center of pressure as an icon on the display; detecting movement of the patient's center of pressure on the surface of the balance plate, with the patient's feet in full contact with the balance plate for the duration of the test; and moving the icon representing the patient's center of pressure in tandem with the movement of the patient's center of pressure detected above the balance plate.

It is to be understood that both the foregoing general description and the following detailed description are exemplary and explanatory only and are not restrictive of the invention, as claimed. In the present specification and claims, the word "comprising" and its derivatives including "comprises" and "comprise" include each of the stated integers, but does not exclude the inclusion of one or more further integers.

The claims as filed and attached with this specification are hereby incorporated by reference into the text of the present description.

The accompanying drawings, which are incorporated in and constitute a part of this specification, illustrate several embodiments of the invention and together with the description, serve to explain the principles of the invention.

BRIEF DESCRIPTION OF THE FIGURES

FIG. 4 is a view of a display of a balance test result using the balance plate of FIG. 1.

FIG. 8 is a view of the display showing the results of the body movement control pathway tests of FIGS. 5 and 7.

DETAILED DESCRIPTION

The disclosed methods and devices may be understood more readily by reference to the following detailed description of particular embodiments, examples of which are illustrated in the accompanying drawings.

Figure 1:
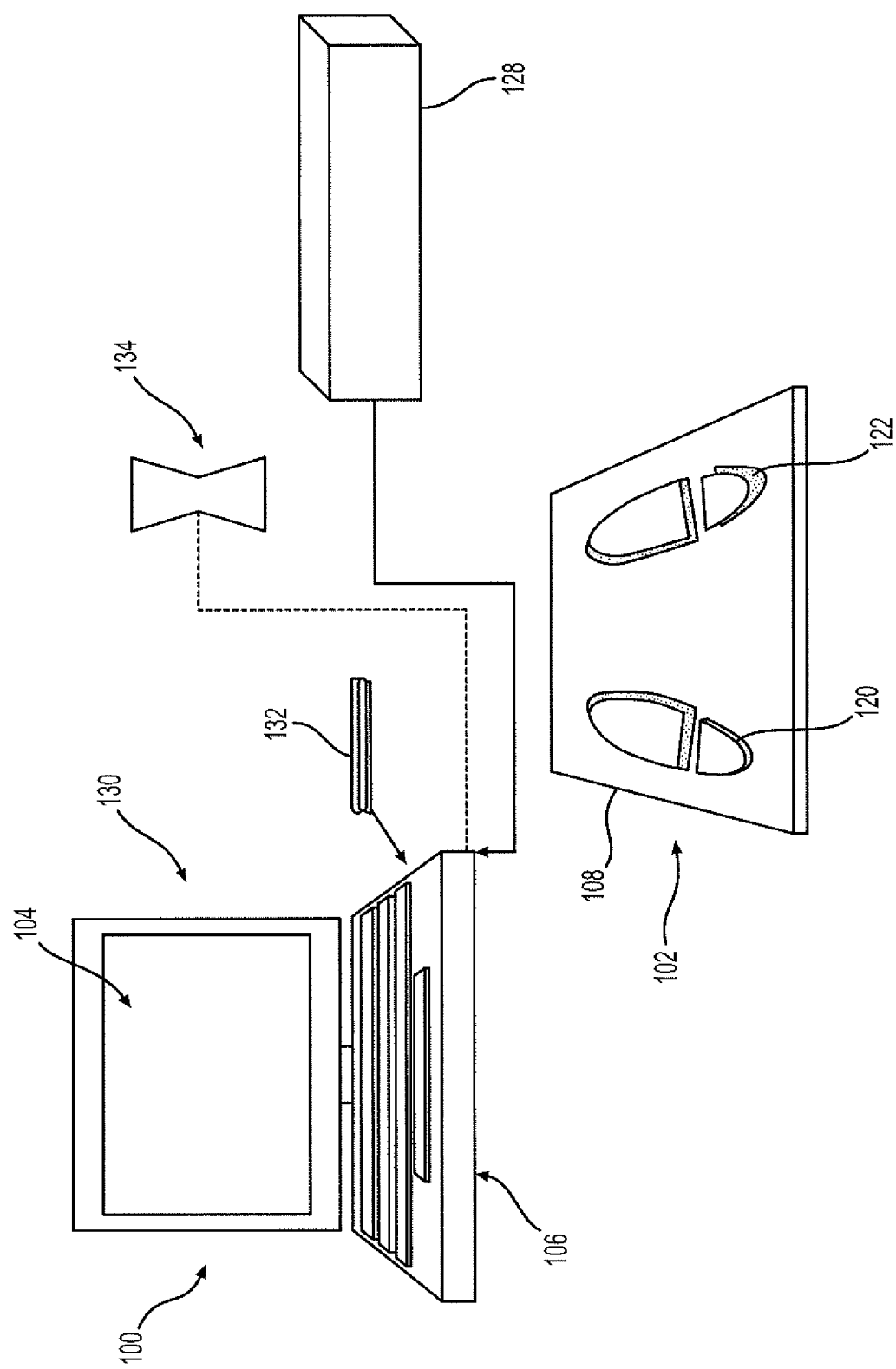
FIG. 1 is a diagrammatic view of a system having a processor, a display and a balance plate.
Figure 2:
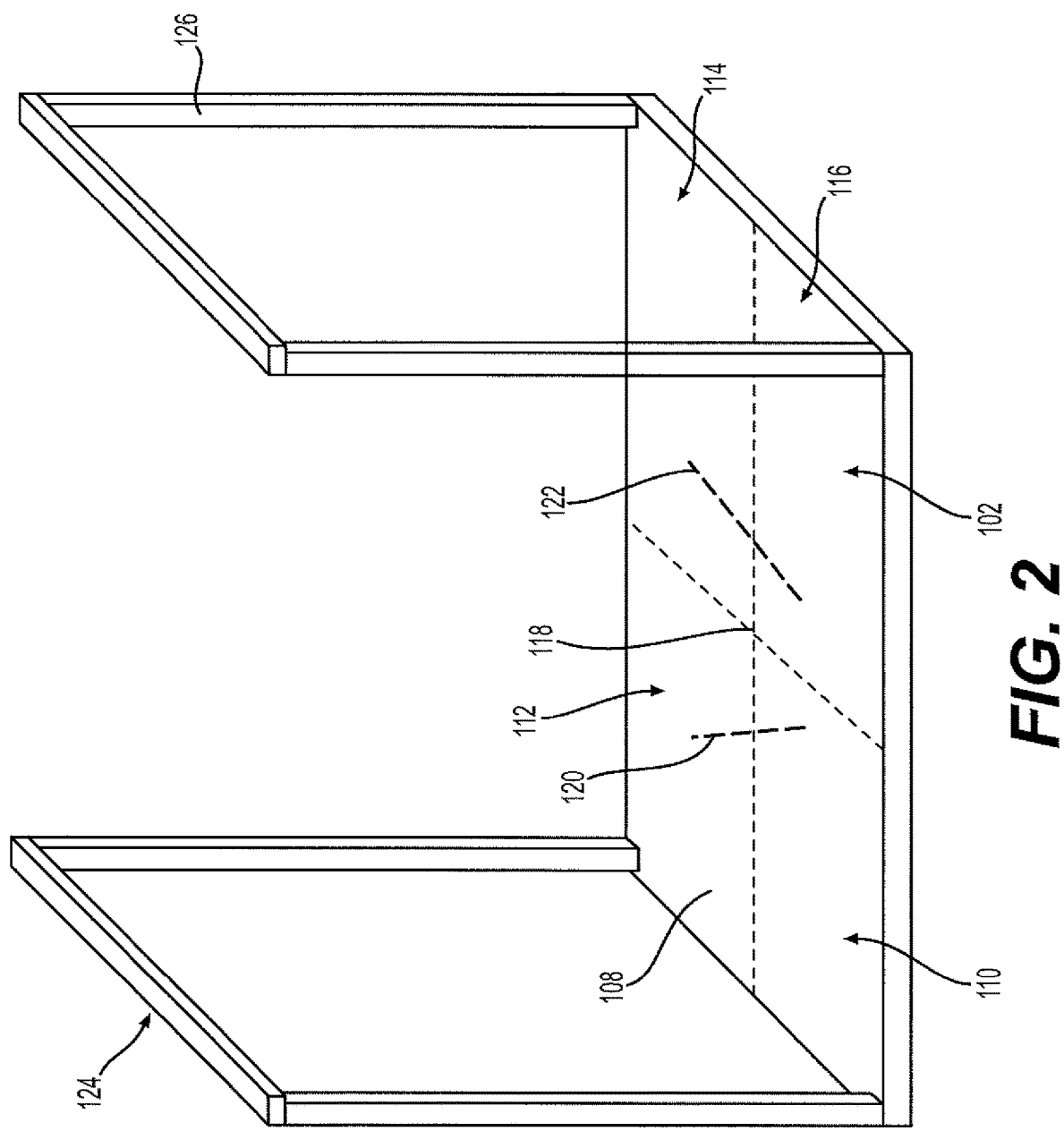
FIG. 2 is a perspective view of the balance plate of FIG. 1 with optional handrails.

FIGS. 1 and 2 show an embodiment of a system 100 having a balance plate 102, visual display 104, and processor 106. In use, a patient or other subject stands on balance plate 102 and performs one or more tests in response to instructions or visual stimuli displayed on display 104. Data, such as Centre of Pressure (COP) data is obtained from balance plate 102 and processed by processor 106 in tandem with the progression of a test presented in display 104. The information can be correlated and used to assist in diagnosing or rehabilitating the patient or subject. Example elements of system 100 and their interrelationships are described below.

Referring to FIG. 2, balance plate 102 can include an upper surface 108 on which the patient stands, and four quadrants 110, 112, 114, 116 which intersect at a centre point 118. The four quadrants and centre point 118 can facilitate correct positioning of a patient's feet on plate 102. Balance plate 102 can also carry demarcations 120, 122 to assist a patient to position his or her feet correctly. A purpose of the demarcated quadrants 110, 112, 114, 116 or the foot positioning guides 120, 122 or both is to ensure that a centre of gravity of the patient is vertically aligned with the centre point 118 when the patient is motionless. However, the balance plate design is such that the patient does not have to stand in a perfectly centered position for accurate data collection. Provided that the patient's COP is within, for example, a 0.8 inch diameter circle as displayed on a display screen within the patient's field of vision, accurate balance data is collected. This may require minor adjustments of the patient's foot positioning at the commencement of a test. Each quadrant may include a load cell to measure dynamic weight distribution on plate 102 when a patient is standing on the plate. Two guide rails 124, 126 may be included to assist a patient while performing tests on the balance plate or an overhead harness safety support system may be employed with severely balance challenged patients.

The four load cells can each be in the form of a low profile planar beam load cell. Such load cells find application in compact scales, bench and floor scales and retail and counting scales. They also find application in the medical field. In this embodiment, the load cells can be oriented and configured so that the balance plate defines a four-cell balance plate. The data output from the load cells can then be sent out with suitable circuitry to be read to processor 106.

Balance plate 102 may be constructed using one or more Hall sensors if desired, and as an alternative to resistive load cells. Hall sensors use a magnetic principle to detect movement, and are generally considered more accurate.

As can be seen in FIG. 1, balance plate 102 can be connected to processor 106, which can be in the form of a laptop computer 130, with a suitable interface device 128 to facilitate communication between plate 102 and computer 130. Interface device 128 may contain one or more wireless radios with transceivers configured for use with peer-to-peer communications (e.g., Bluetooth and/or Wi-Fi Direct), and/or WLAN communications through a dedicated Access Point. Interface 128 may be configured for wired communications in addition to, or instead of, wireless communications.

For simplicity, processor 106 is described in reference to laptop computer 130, though other configurations can be used. For example, processor 106 may be formed as a variety of mobile and/or stationary computing devices, such as, but not limited to a tablet, a smart device (e.g., smartphone), a desktop computer, and/or a wearable device such as eyewear or bracelet. As would be appreciated by those of ordinary skill in the art, a processor such as described above includes a chip and associated memory. Laptop computer 130 can include wireless communications capabilities, such as one or more wireless radios configured for communication via a peer-to-peer communications technology (e.g., Bluetooth and/or Wi-Fi Direct) and/or non peer-to-peer communications such as WLAN.

As shown in FIG. 1, system 100 may include a removable memory, such as removable memory 132, for example formed as a USB memory device. It will be appreciated that data may be stored in a variety of ways, for example, in the hard disc of laptop 130, USB 132, one or more remote servers, and/or the Cloud.

As shown in FIG. 1, display 104 can be operatively (and physically) connected to processor 106. It will be appreciated that the display may be configured as a separate, stand-alone device. For example, the display may be a television or computer monitor with a detachable wired connection, and/or wirelessly connected to laptop 130. The display may have a touchscreen if desired. The display may be positioned near the periphery of balance plate 102 and at a height sufficient to permit the patient to easily see the screen. To facilitate differing heights of subjects, the display may be mounted on an adjustable stand attached to, or separate from balance plate 102.

Figure 3:
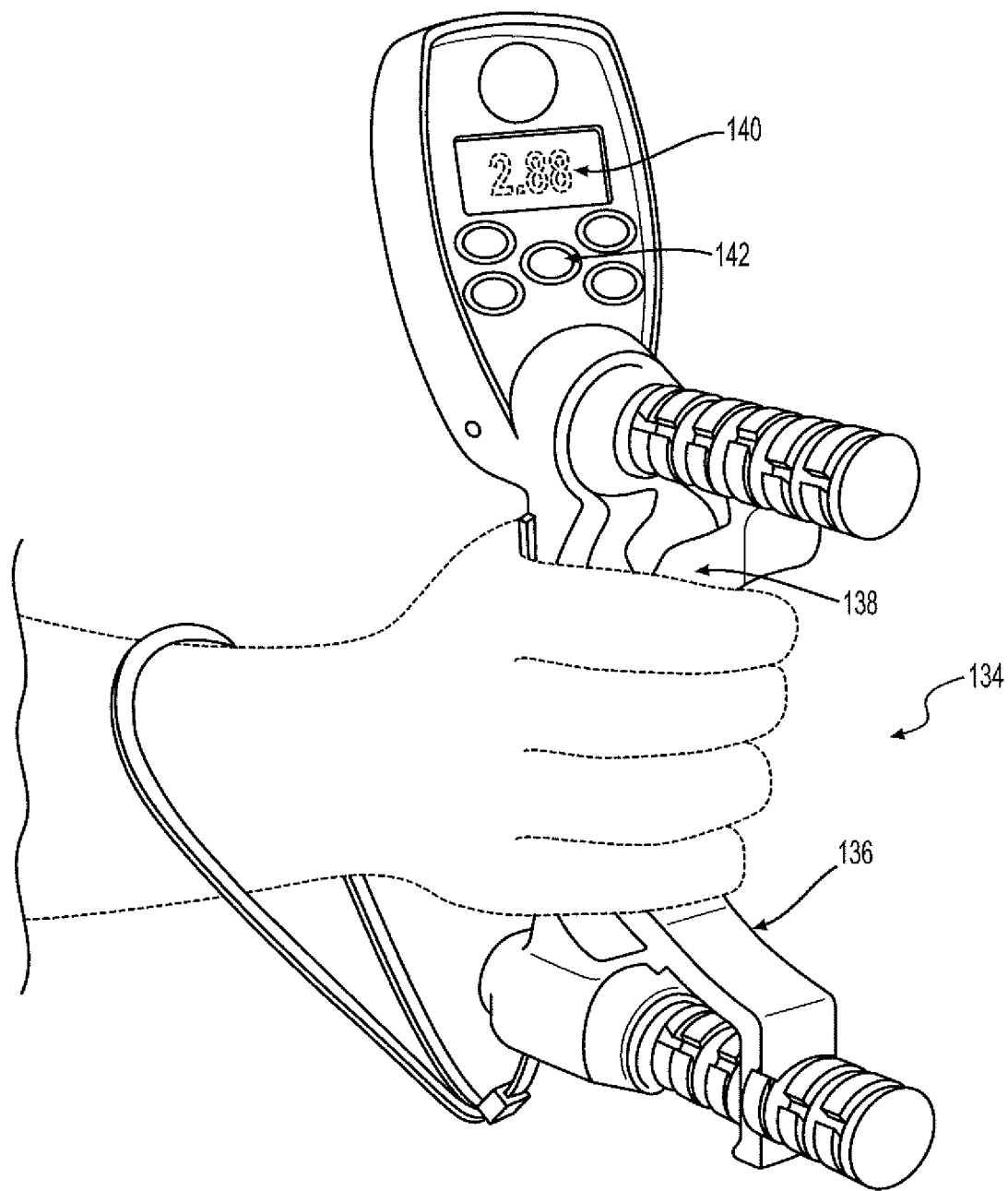
FIG. 3 is a perspective view of a hand dynamometer for use in determining fine motor control of a patient.

FIG. 3 shows a hand dynamometer 134 configured to measure pressure exerted by the subject over a timed duration. Dynamometer 134 includes a handgrip 136, a handgrip pressure sensor 138, a visual display 140, and a user interface 142. Dynamometer 134 may be used for testing a subject's fine motor control capabilities. Dynamometer 134 may further include a wireless communications transceiver configured to communicate with laptop 130. The transceiver may be configured for peer-to-peer communications and/or WLAN similar to transceivers already described above.

Figure 4:
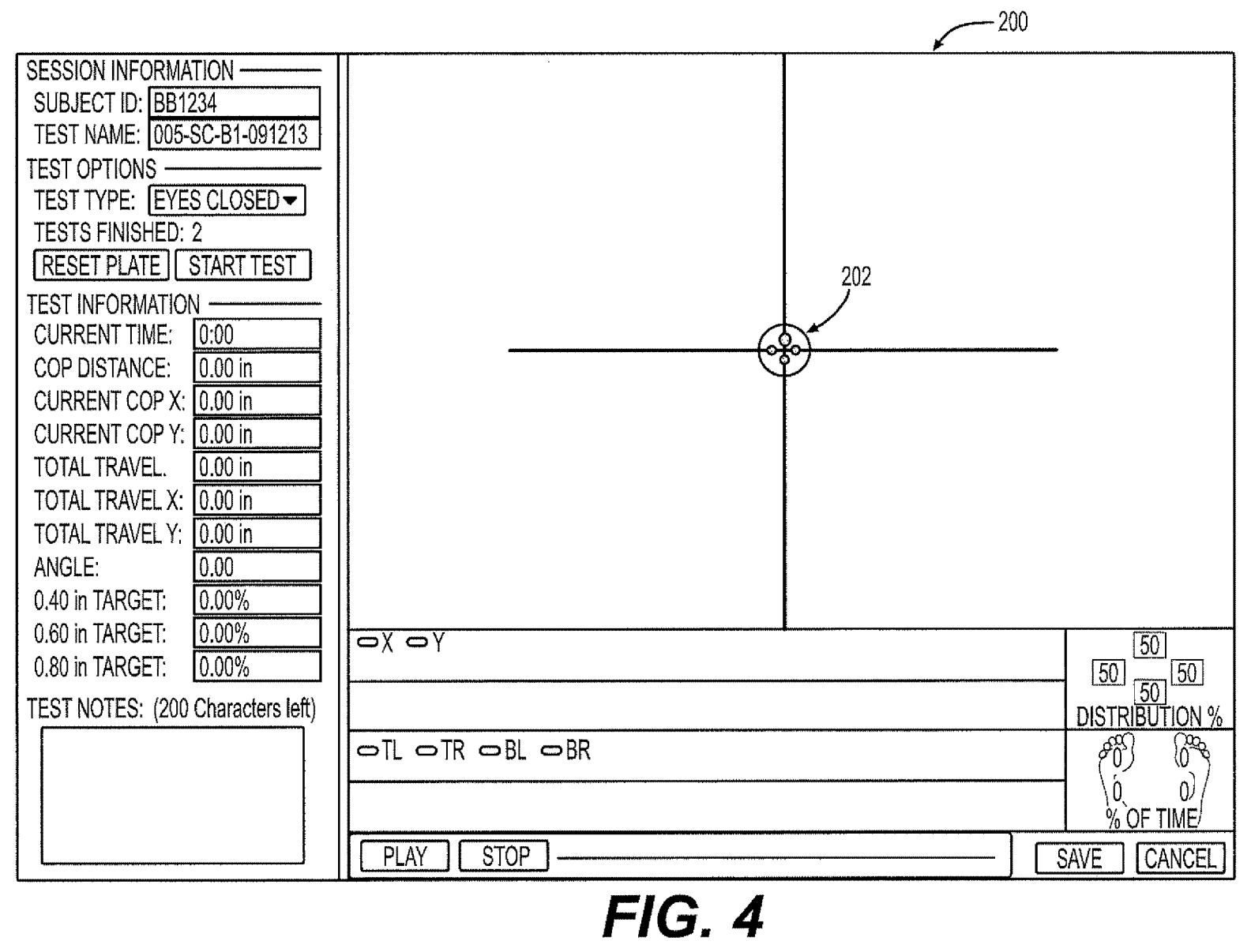

The components of system 100 may be configured for use with a variety of tests. Referring to FIG. 4, a balance test may be conducted to diagnose and/or facilitate rehabilitation of the patient. The patient stands on balance plate 102. The patient can be static or stationery on balance plate 102, or can carry out various actions depending on the type and level of analysis required. Data from balance plate 102 is communicated through interface 128 to laptop 130. Processor 106 presents the balance data on a screen 200, with the patient's COP shown as a dot or icon 202. Various data may be obtained through the balance test, such as, but not limited to sway velocity and entropy data. In some cases, a first test is conducted with eyes open, then a second test with eyes closed. The balance test is useful for treating balance disorders, including treatment for ear infection, stroke, multiple sclerosis, Dementia, Alzheimer's, spinal cord injury, Parkinson's Disease, neuromuscular conditions, acquired brain injury, cerebellar dysfunction, and/or ataxia. The balance test can also be beneficial in assessing fall risk in the elderly, as hip fracture after a fall puts a person at a very high risk for stroke, premature disability and ultimately death. An example, a system and method for using balance data to identify and treat a patient is shown and described in International Application No. PCT/AU2014/000149, the entire contents of which is incorporated by reference herein.

Though the balance test is a useful tool, at least for the reasons mentioned above, determining a subject's balancing ability in combination with one or more additional assessments is a more useful tool to identify physical and/or mental disorders, and track the progress of rehabilitation in situations where a subject is recovering from an injury. Additional assessments include a subject's body movement control, capacity for planning and foresight, and cognitive abilities. For example, for ascertaining and measuring body movement control, system 100 may be configured to present a test to the subject in which the subject, while on balance plate 102, attempts to control their COP, depicted as an icon on the screen of display 104, from a first fixed point to a second fixed point. Balance plate 102 can measure the COP of the subject and communicate the COP data to laptop 130, which can be configured to graphically depict the subject's COP as an icon on the display screen. Several variations of a combination balance/body movement control test have been developed, as will be described in further detail below.

Figure 5:
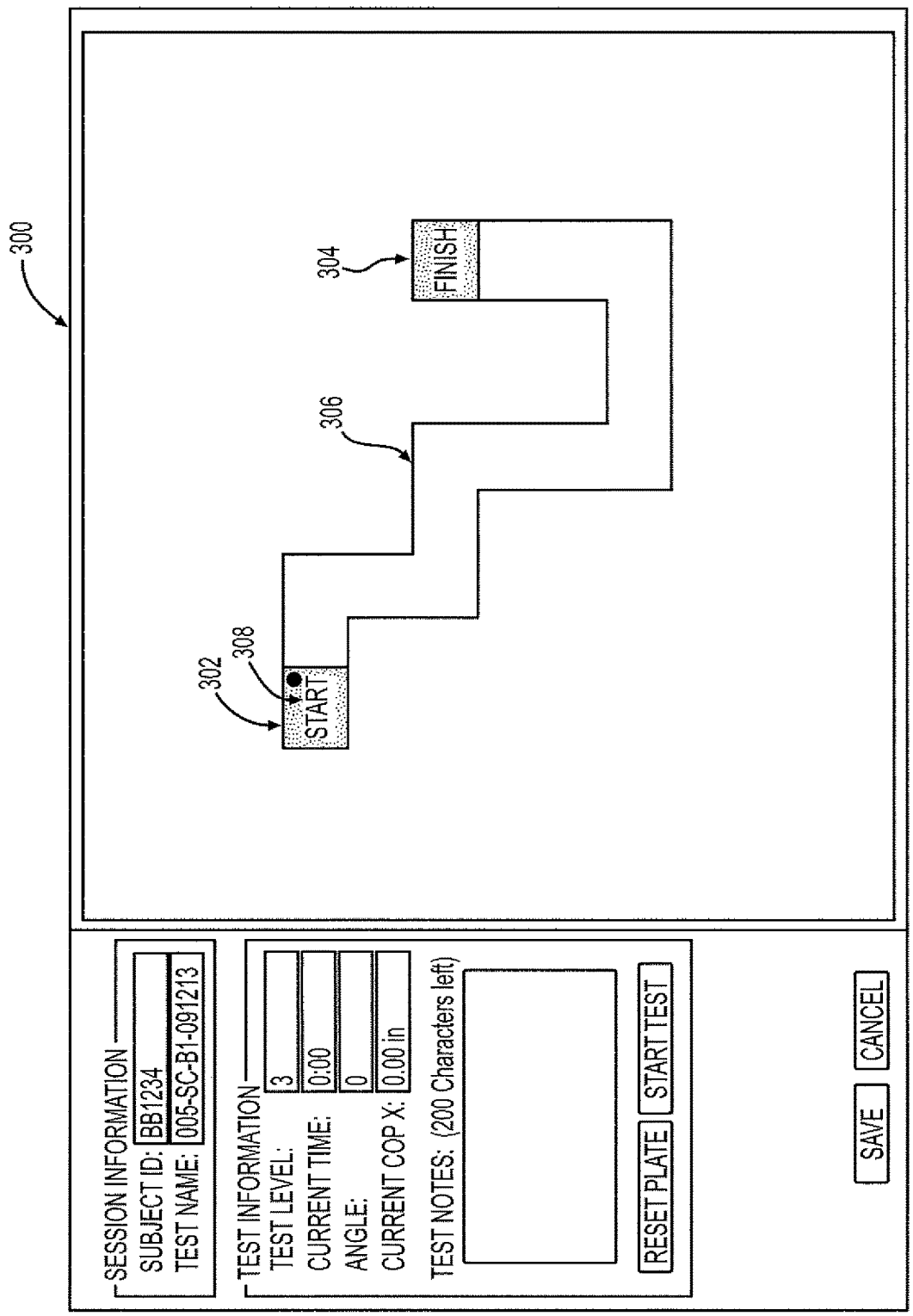
FIG. 5 is a view of a display showing the starting and finishing points of a first body movement control pathway test used in the system of FIG. 1.
Figure 6:
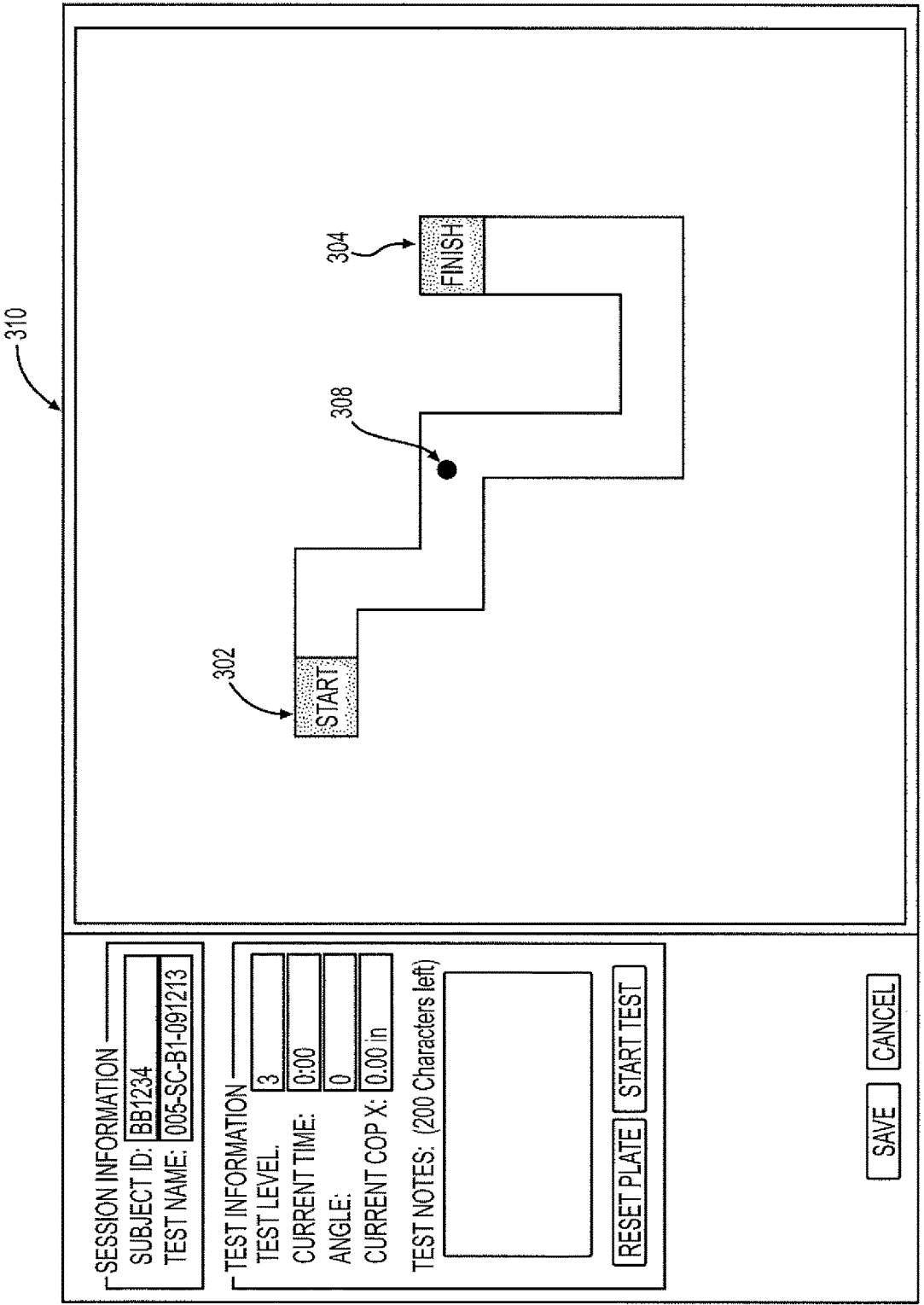
FIG. 6 is a view of the display of FIG. 5 showing the progress of an individual toward the finishing point of the first body movement control pathway test.
Figure 7:
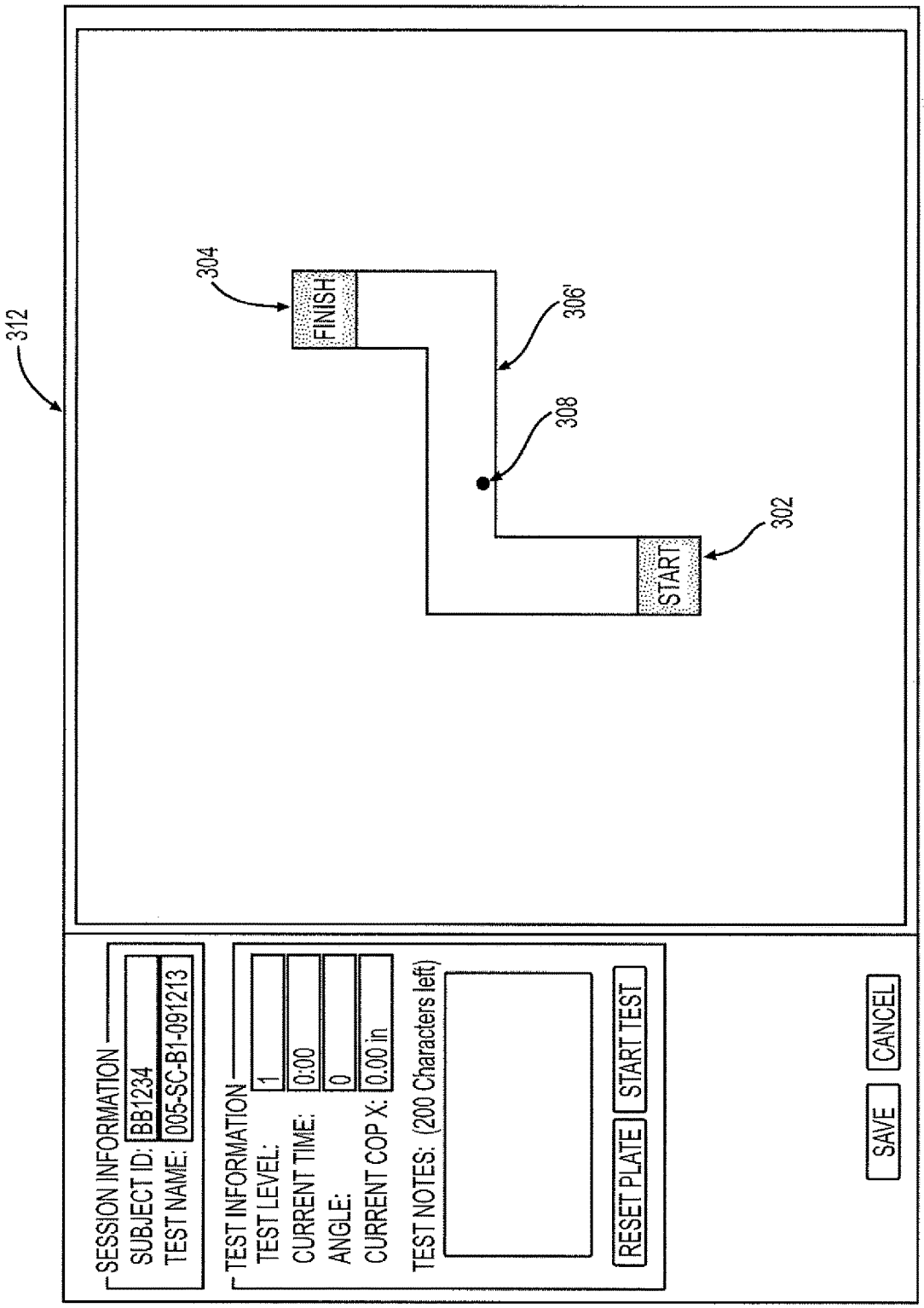
FIG. 7 is a view of a display showing a second body movement control pathway test.

FIGS. 5-9 show a body movement control test in which the subject attempts to guide their COP through a pathway. Referring to FIGS. 5 and 6, the subject, while on balance plate 102, controls their COP, as depicted by an icon 308, from a first, predetermined starting position 302 to a second, predetermined finishing position 304 along a pathway 306, as shown on screen 300. In order to facilitate the display of the subject's COP, processor 106 can be configured to portray the subject's COP as icon 308 moving across the screen of display 104 in tandem with the movement of the subject's COP detected and measured by balance plate 102. FIG. 6 shows the subject's COP traversing approximately half the distance along the pathway on screen 310. As shown in FIG. 7, a second test may be conducted with a differently configured pathway 306' shown on screen 312. During each test, processor 106 is configured to time the test and to track movement of the subject's COP, as measured by balance plate 102, relative to a coordinate system for determination of the extent of variation of the subject's COP during the progress of the test. The timing may be in relation to how long it takes the subject to conscientiously move their COP from the first fixed point to the second fixed point, or may be within a predetermined time period. To facilitate timing of the test, processor 106 may include a timing circuit or tinier. The data may be graphically displayed as further described below. The number of 'collisions' with the pathway walls and the time taken to resume a correct controlled movement in the desired direction for completion is additionally computed.

Figure 8:
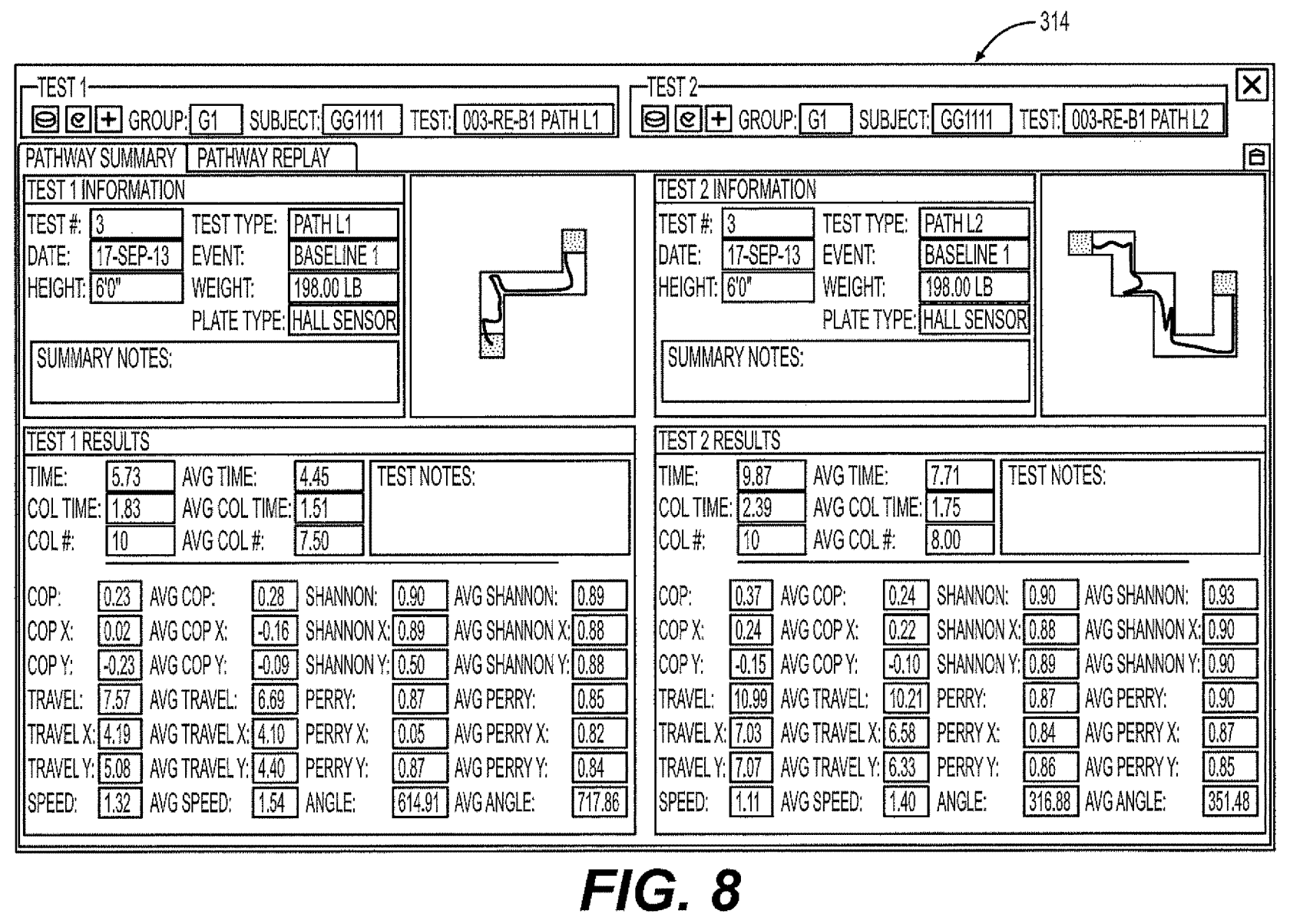
Figure 9:
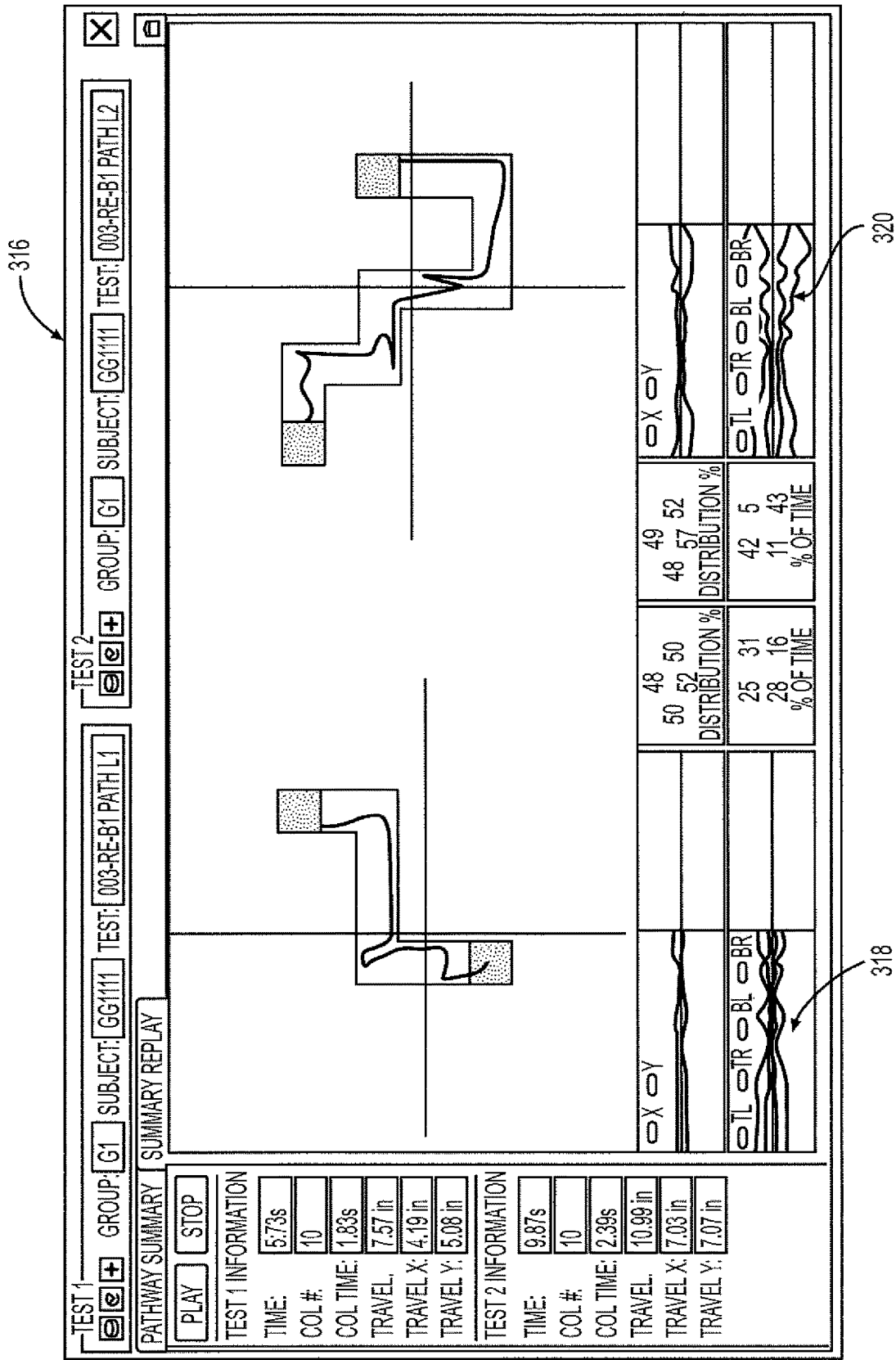
FIG. 9 is a view of the display showing an expanded view the graphical results of the body movement control pathway tests of FIGS. 5 and 7.

Referring to FIGS. 8 and 9, the results of each pathway test can be graphically displayed on screens 314, 316. Traces 318, 320 of each test may be visually presented to show the extent of COP movement relative to time. The resultant data may be used to diagnose and treat mental and/or physical disorders, and/or ascertain progress with patient rehabilitation. The resultant data may be associated or stored in an electronic record of a patient profile stored on an electronic database configured to store a plurality of patient profiles. Each patient profile may include one or more records relating to a test result. Processor 106 may be configured to compare the records or results of a single patient, and/or compare test results among a plurality of patients to develop a diagnostic database of COP profiles having characteristics generally matching a COP profile of a patient with a known physical and/or mental disorder. Comparisons conducted by processor 106 for a single patient may also be used to track a patient's progress during rehabilitation. Comparisons between a single patient relative to a standardized set of data may be conducted to ascertain how the patient is performing relative to a general population or specific subgroup—for example by age or gender.

Figure 10:
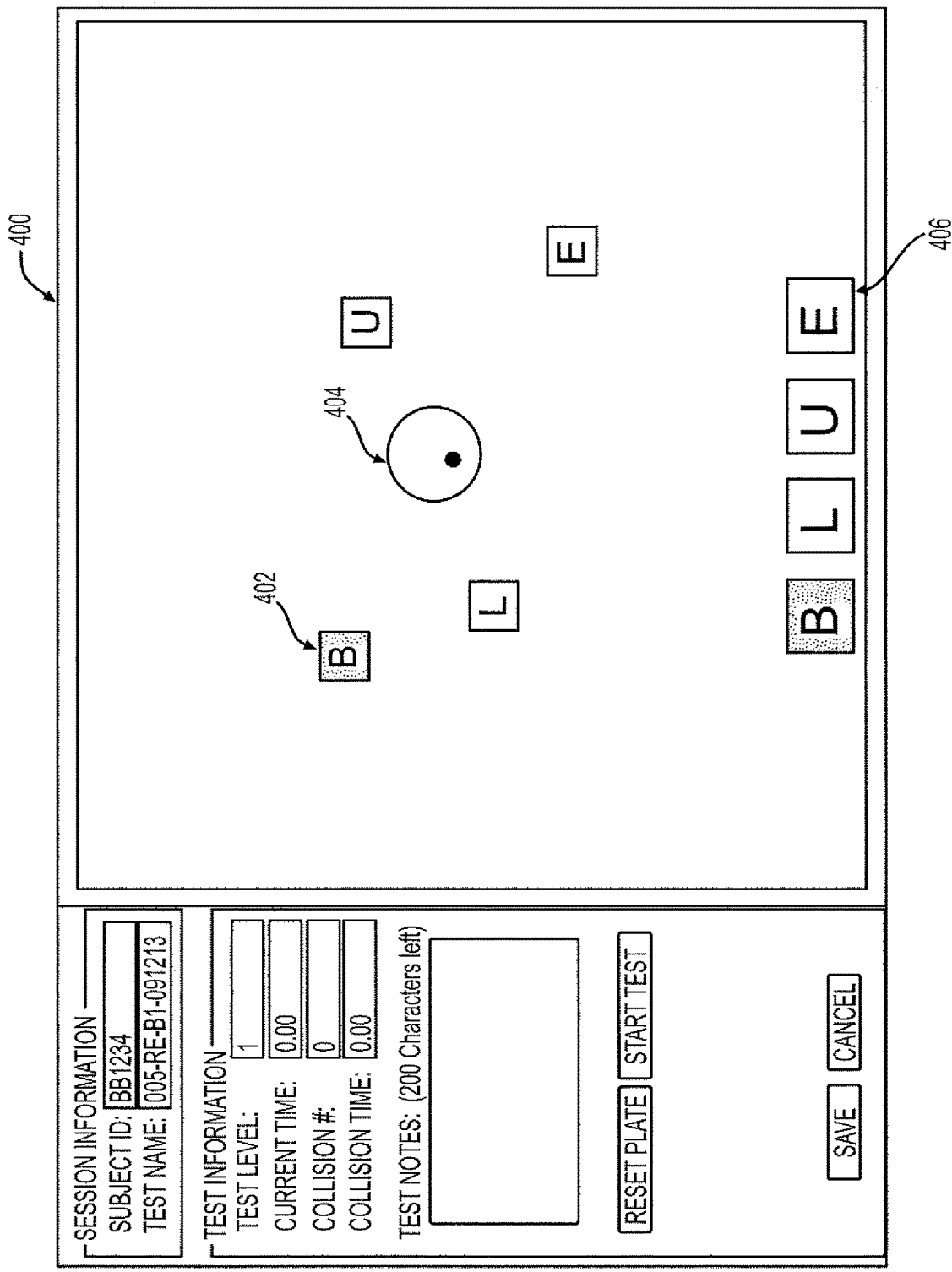
FIG. 10 is a view of a display showing a series of letters for spelling a word for a body movement control spelling test used in the system of FIG. 1.
Figure 11:
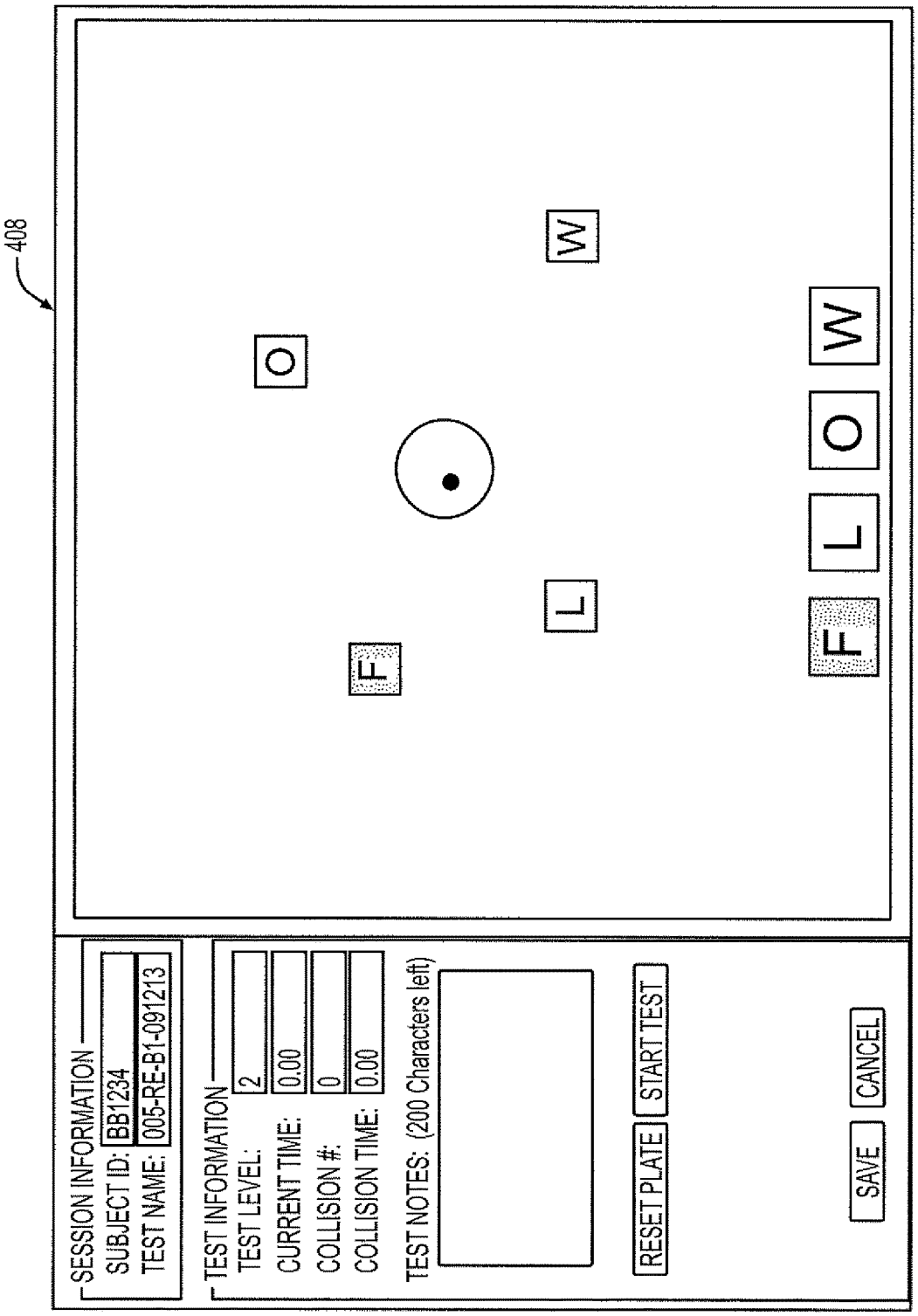
FIG. 11 is a view of a display showing a series of letters for spelling a word for a second body movement control spelling test.
Figure 12:
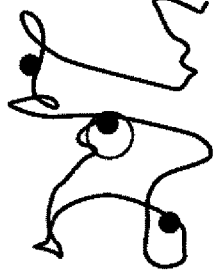
FIG. 12 is a view of the display showing the results of the body movement control spell test of FIG. 10, and a second body movement control spell test.
Figure 13:
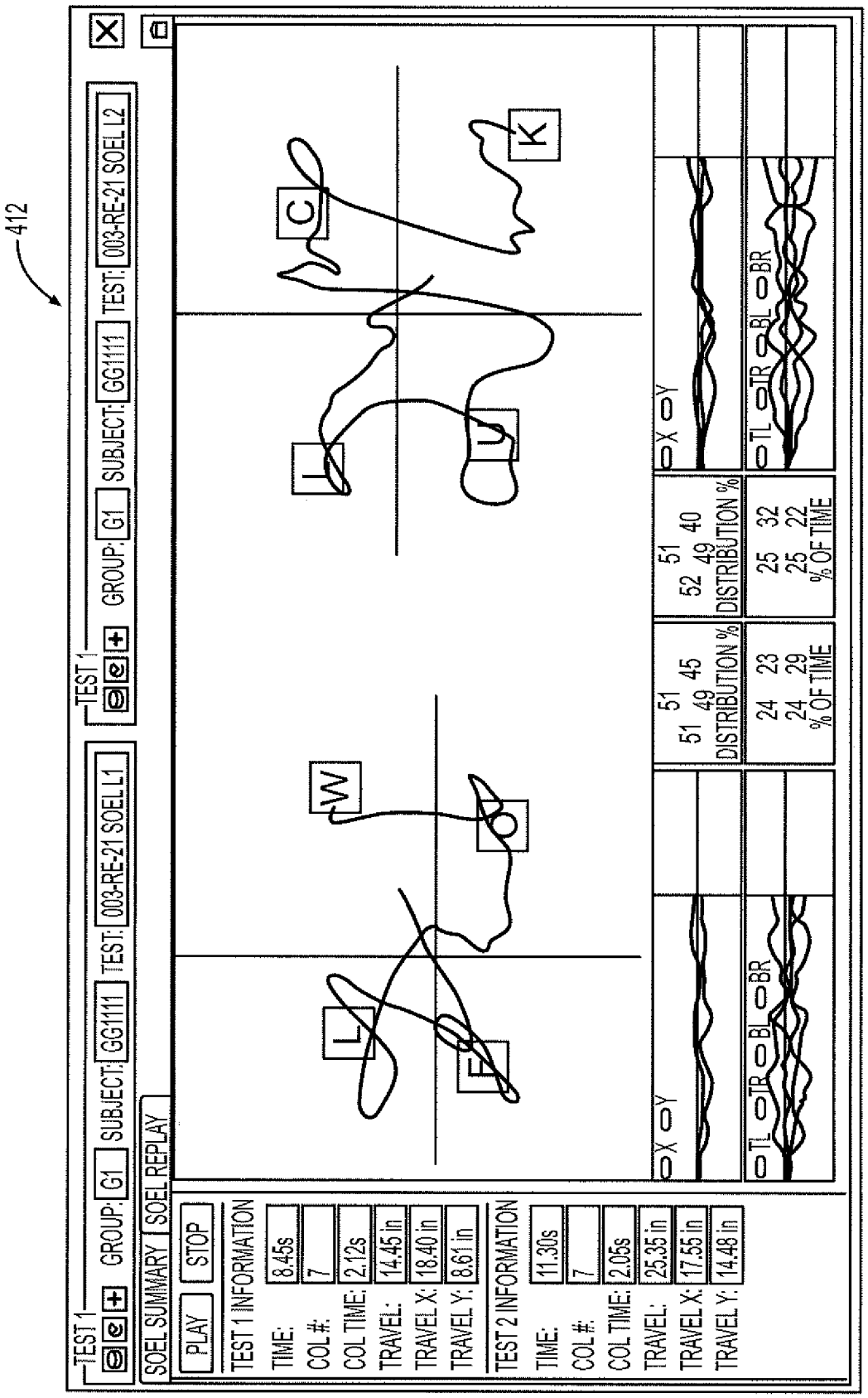
FIG. 13 is a view of the display showing an expanded view the graphical results of the body movement control spell tests of FIG. 12.

Referring now to FIGS. 10-13, a further body movement test is shown and described in which a subject uses their COP to spell a recognizable word. As used herein, a "recognizable word" is one which would appear in a commonly accepted dictionary. As shown in FIG. 10, the subject moves their COP, as represented by icon 404 on screen 400, from a central position towards a letter 402 in order to spell a recognizable word from a plurality of letters on screen 400. In the example shown in FIG. 10, the recognizable word is BLUE. Processor 106 can be configured to track the movement of the subject's COP as the subject attempts to move their COP, represented by icon 404, from letter to letter in an order which will spell out the word. Referring to FIG. 11, screen 408 shows a second body movement control spell test using the word FLOW. Words with two to five letters are preferred, though more letters may be used if desired. The letters can be specifically placed in the patient's field of vision on the screen to maximize the challenge to the patient in spelling out the word using the letters. Varying levels of increasingly difficulty of challenge are used for pathway and spell assessment testing. As with the body movement control pathway test described above, processor 106 may be configured to graphically present the results of each spell test, for example, on screen 410 (FIG. 12) and/or screen 412 (FIG. 13). As shown at the bottom of screen 412 in FIG. 13, the results may be presented as a trace showing the extent of variation of the subject's COP over time.

Figure 14:
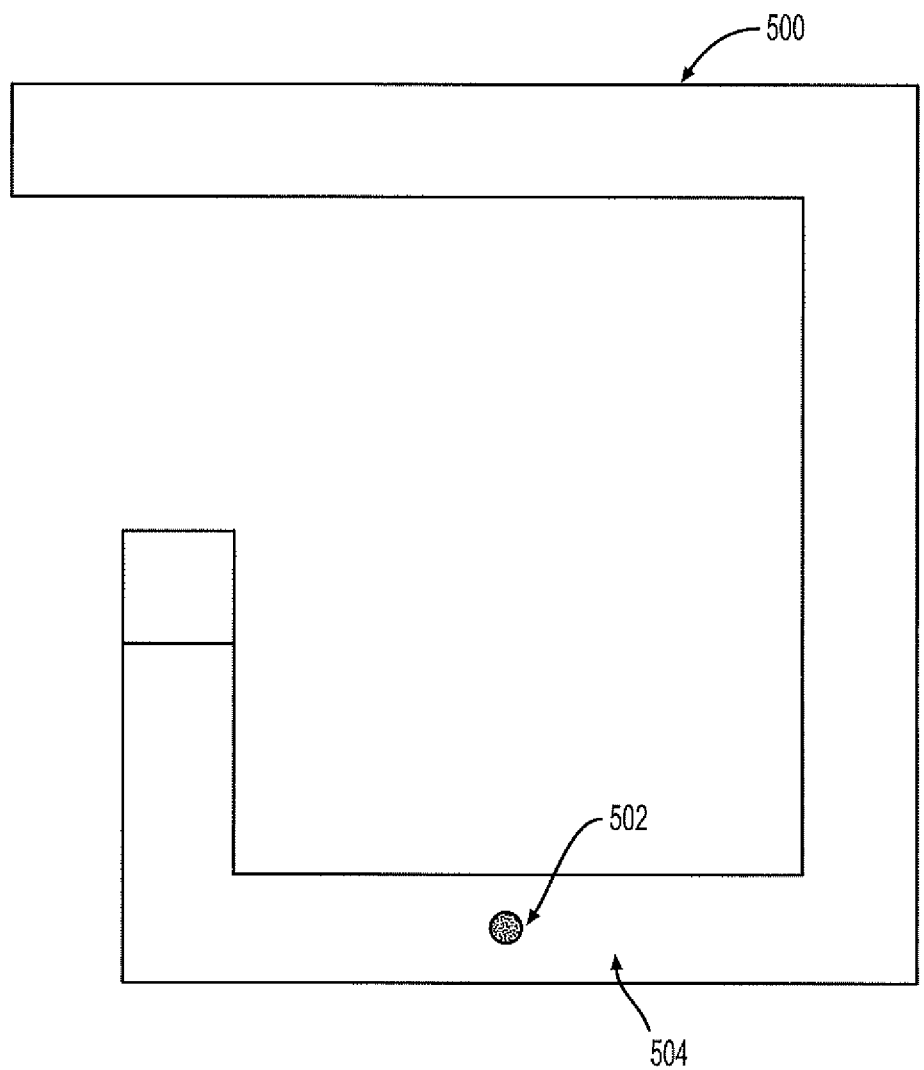
FIG. 14 is a view of a display showing a first maze test for evaluating the patient's capacity for planning and foresight.
Figure 15:
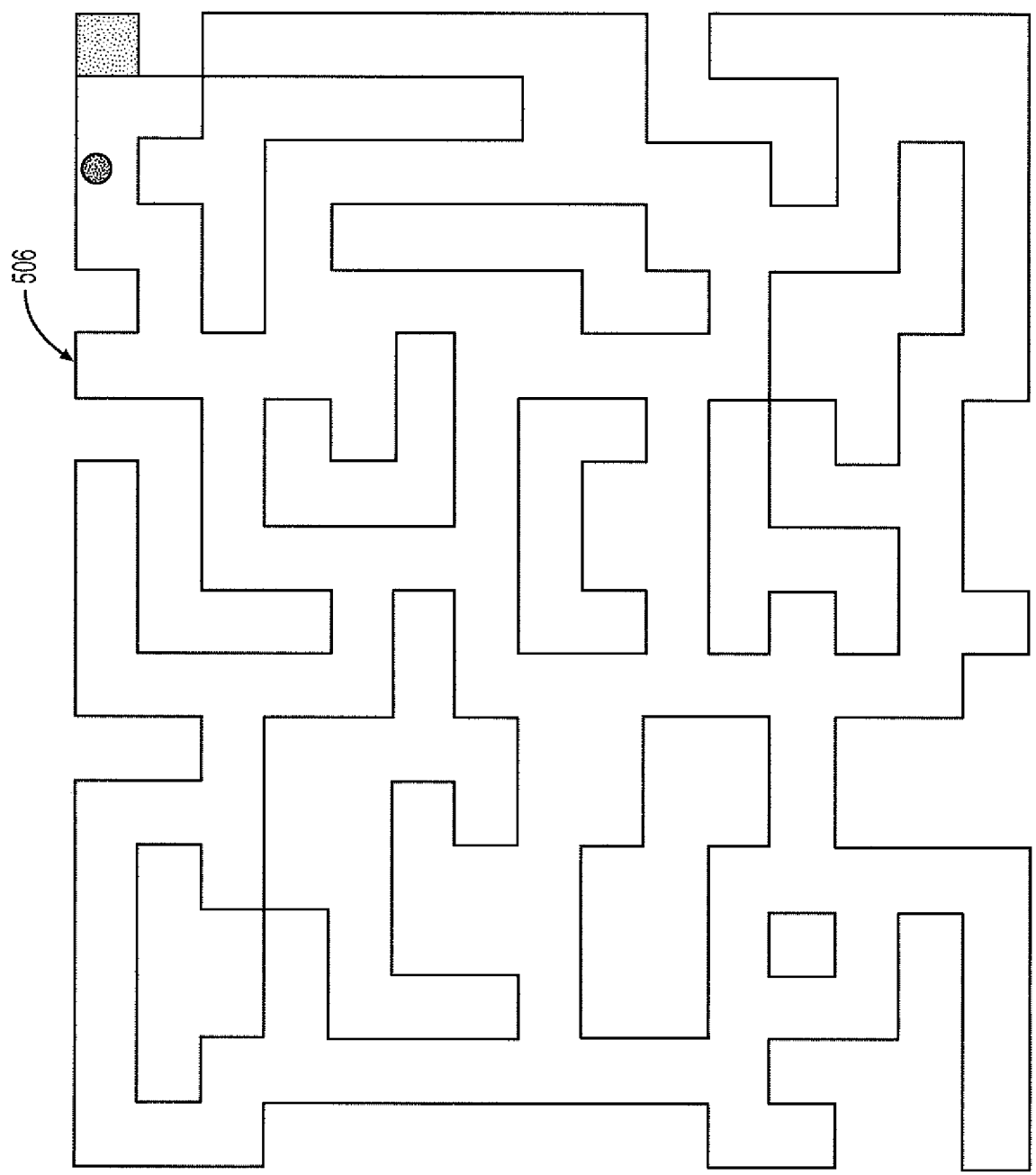
FIG. 15 is a view of a display showing a second maze test for evaluating the patient's capacity for planning and foresight.

Another useful test to diagnose mental and/or physical disorders, or track rehabilitation is to measure a patient's capacity for planning and foresight. One way to measure a patient's capacity for planning and foresight is through a maze test. Referring to FIGS. 14 and 15, a subject may use the user interface of a computer or peripheral device to guide an icon 502, shown on screen 500, through a pathway 504 of a maze. Completion of the maze can be marked by the subject's arrival at the "end point." The participant's score can be calculated by automatically summing the subject's errors including bumping into the sides of the maze and the time to complete the assessment and move dot 502 from start to finish. This assists in determining the subject's ability to plan and co-ordinate the dot movement. Results of this test can be determined by comparing an assessment with a baseline composite or average score for this, subject using a minimum of three baseline tests. An example of a further maze test is shown in FIG. 15 on screen 506. Subjects who scored high with a significantly higher number of wall collisions and longer time to complete the test indicate qualities related to poor planning and foresight. High scores also relate to differences in verbal and performance intelligence.

More definitive comparisons are available as the subject is tested further with increasingly more difficult maze designs. Each additional test can be added to the subject's cumulative baseline, e.g., up to ten tests. To preserve the currency of subject data and minimize maturation, the last (most recent) tests (e.g., most recent ten tests) for each subject can be averaged for this subject's updated baseline. Subjects may be compared, within subject, subject to subject, subject to selected groups, e.g., by age or gender, or specific subgroups as specified in the customized data collection by the clinician or researcher. All subject data can be de-identified and stored in an encrypted form on a multi-level security Cloud to comply with applicable national privacy laws such as HIPAA and other electronic medical record storage requirements.

The initial test may be discarded in each test session to allow either for a learning factor or an abnormal situation occurring during the test. "High" scores show lots of collisions and a long test duration.

In an experiment, participants were asked to trace their way through a complex network of passages for which the participant must find a route that will bring them to an exit point. Participants were cautioned to not cross through solid lines with their "pen." Participants were expected to implicitly scan the maze viewing the pattern and determine a successful way to maneuver through the passages to the exit point. Entering a "blind alley" was a terminal error that resulted in the ending of the test. Participants were then allowed to repeat the same maze with a deduction to their scoring. The particular level of difficulty of the test determines the typical number of failed attempts that will end a subject's trial. The number of trials required to complete a given maze proves a measure of the skill to be "beneficial"; based on the system feedback and what has been learned from previous errors. The number of seconds to finish each maze can be seen as an indicator of cognitive efficiency as well as a marker of random acts, since time may be spent on fast, but incorrect decisions.

Mazes in general are thought to assess procedures such as selection, trying, rejection, or adoption of alternative sequences of conduct or thought.

Processor 106 may be configured with a countdown function, which will advise again of when the test will start dot 502 moving. A goal is to direct dot 502 to the end (Finish Point) of the maze preferably without hitting any wall or making any wrong turns.

An assessment for fine motor control can use hand dynamometer 134, shown in FIG. 3. A user can grip dynamometer 134 and performs a series of exercises according to a prescribed applied pressure level for a prescribed duration of time. This may be small pressures such as ounces up to larger pressures of pounds or multiple pounds and time durations of seconds up to one minute. For return to play situations in sporting activities, a series of three tests can be utilized. The player's ability to comply with the force and duration of time specified in the test can be analyzed and displayed subject within subject, and subject to subject or subject to peer group. Pressure sensor 138 can detect changes in pressure from the user's grip and data can be sent to processor 106 through the transceiver in dynamometer 134. Processor 106 can correlate the data from dynamometer 134 with the progression of the test to arrive with the test results, which may be graphically displayed in a manner similar to that already described. It will be appreciated that the maze test and/or use of hand dynamometer 134 may be used without balance plate 102.

Figure 16:
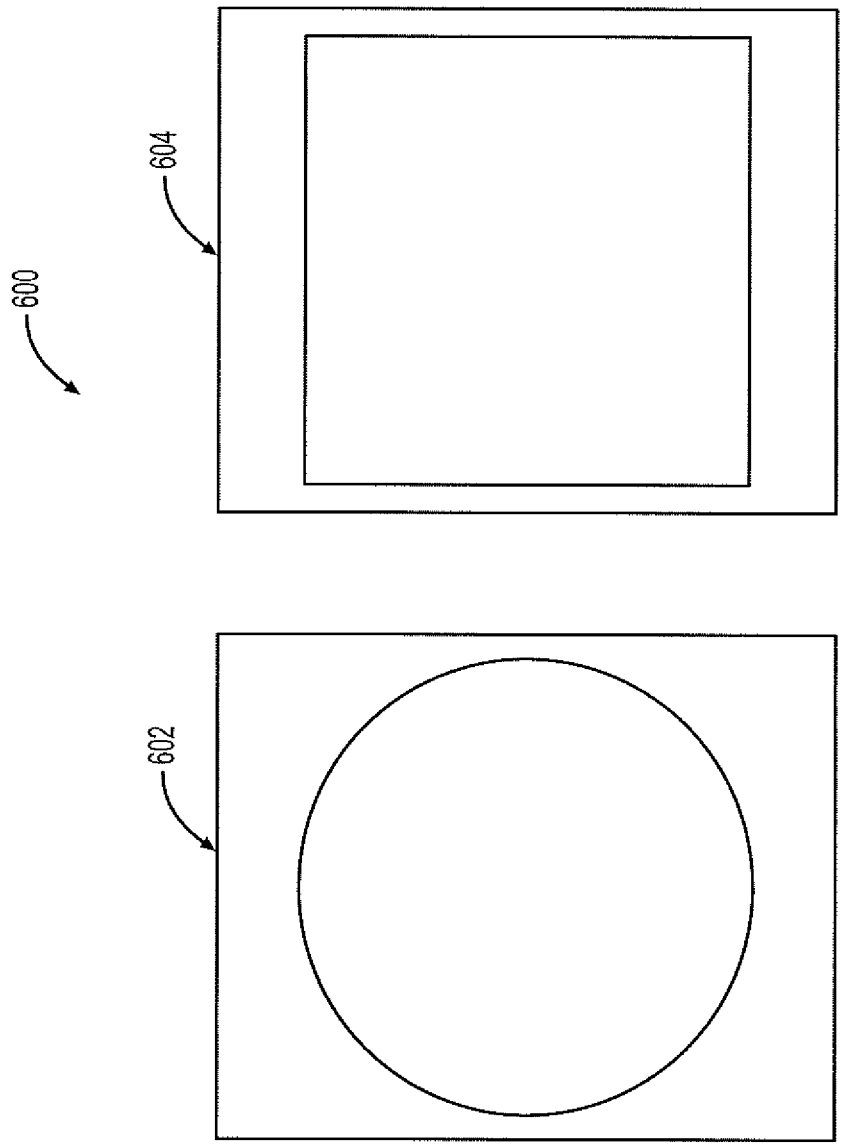
FIG. 16 shows a sample pattern recognition test for cognitive assessment.
Figure 17:
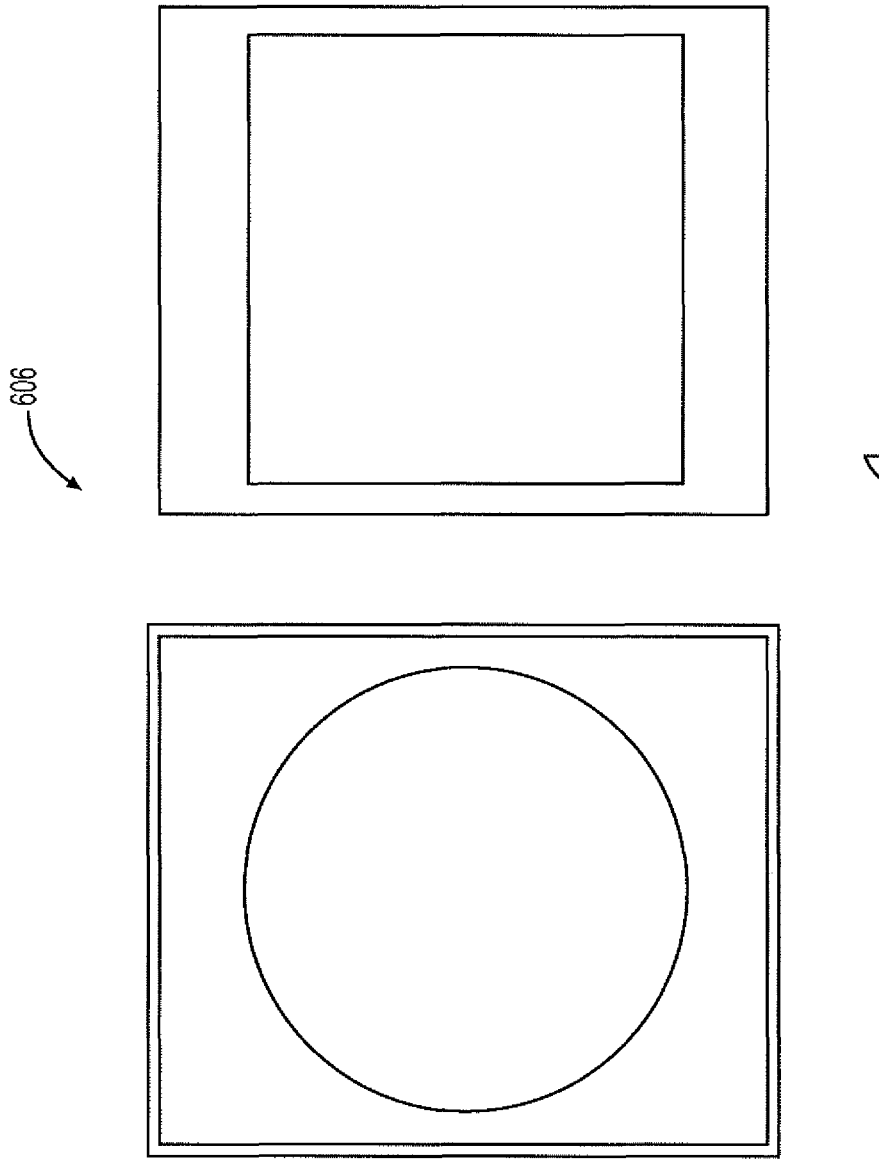
FIG. 17 shows a progression in the test shown in FIG. 16.

Another useful test in combination with a balance assessment is cognitive testing. One example form of cognition assessment utilizes a "Choice" cognitive test. A sample Choice test is illustrated in FIGS. 16 and 17, and utilizes a set of tests designed to test the subject's ability to determine, memorize and recall the pattern of two symbols. A user interface, such as the arrow keys of a keyboard, (right and left), can be used to choose the specific symbol. An example first task is to determine a pattern; for example, two distinct symbols with different shapes of different colors can be shown. In FIG. 16, these shapes are a circle 602 and a square 604 shown on screen 600. The subject can use the left or right arrow keys on a keyboard, or touches the appropriate location on the touchpad, touch screen, or smartphone to make a selection. The system can display if the subject has selected the correct symbol or not. FIG. 17 shows an example on screen 606 where the subject has chosen the correct symbol. An example second task is to recall the set of patterns discovered in step one to assess short term memory. The response times and selections can be evaluated and displayed in a graphed format and in a comparative display weighted against a database average. The Choice test can test elements of both fluid and crystallized intelligence. Fluid intelligence typically involves analytical reasoning. Crystallized intelligence typically involves accumulated knowledge from past experience.

Other cognitive tests may be used. For example, a series of letters forming a pattern may be used to test memory recall. When using shapes such as described above, more than two shapes and colors may be utilized, or a pattern of more than two of the same shape or color may be utilized where desired.

Figure 18:
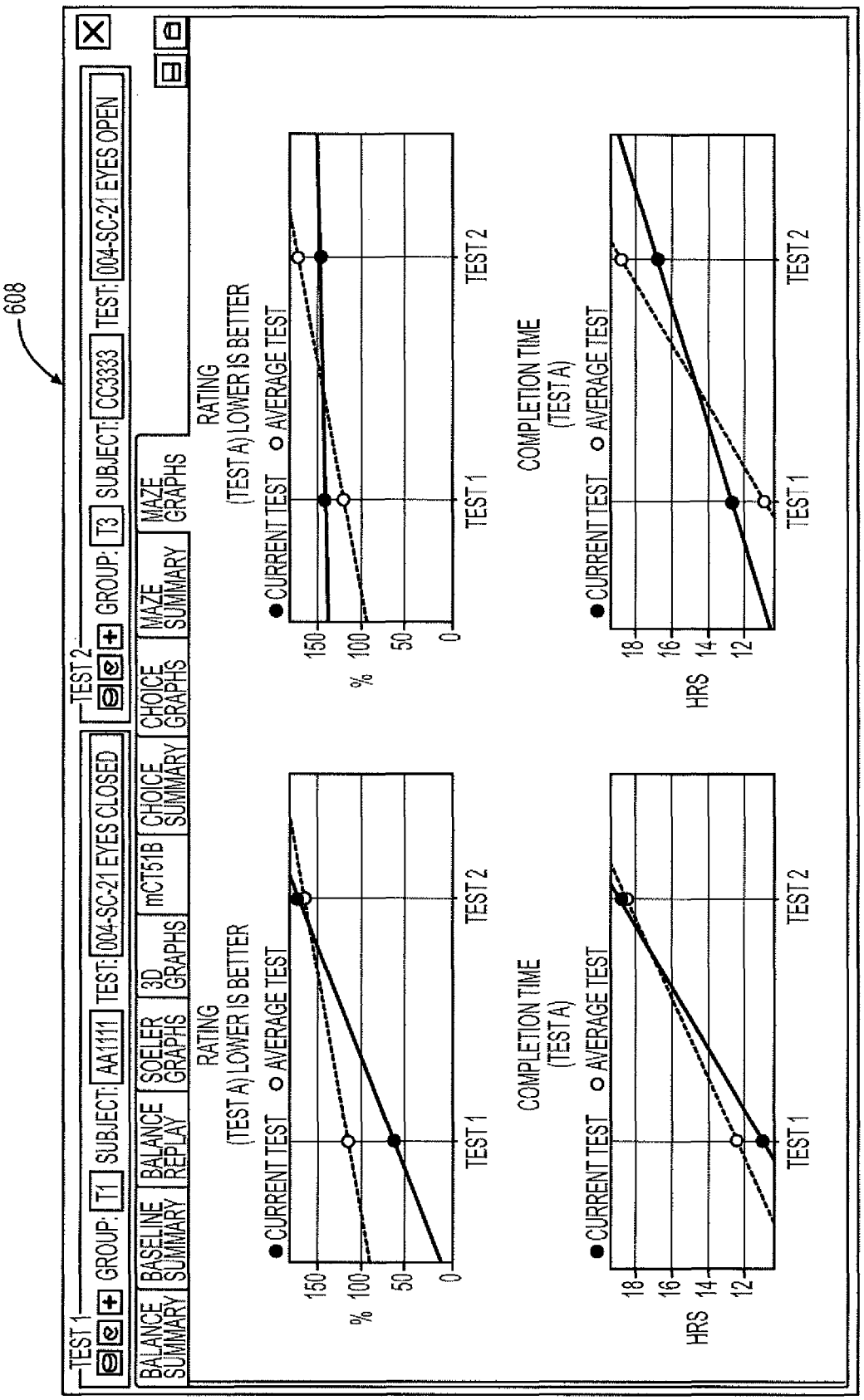
FIG. 18 is a view of a results graph screen displaying the compared results of a maze test for an individual relative to an average set of data.

Referring to FIG. 18, a number of test results may be displayed for easy comparison including: accuracy, total time and rating. For example, for evaluating a maze test result, the Maze Test Rating can be calculated using the main test measurements (total test time, subject inputs, wall collisions and collision time) to produce a score/rating, which represents the quality and overall result of the test in one figure. For example, a lower rating can be a better score.

The accuracy of the maze tests can be calculated by the percentage of time not spent on a maze wall divided by the total time. For example, if a subject spends 5 seconds moving alongside the walls out of a 20 second test, they can get a 75% accuracy. So maze accuracy can be considered the effectiveness of the subject's planning, foresight, proprioception and reflexes operating in a combined manner. Exemplary point allocations may include: each collision event adds 10; each second of collision adds 10; each input adds 3; and each second of test time adds 3.

Trend analysis of the Choice and Maze tests can also be performed in the cognitive graphs screen as shown in FIG. 18.

Referring still to FIG. 18, screen 608 shows that a particular subject is performing above average with their rating. However, the completion time for the subject in test 2 is below the system average. The subject test is compared to the system average, which is derived from all tests that have been recorded by all subjects on a particular system.

Figure 19:
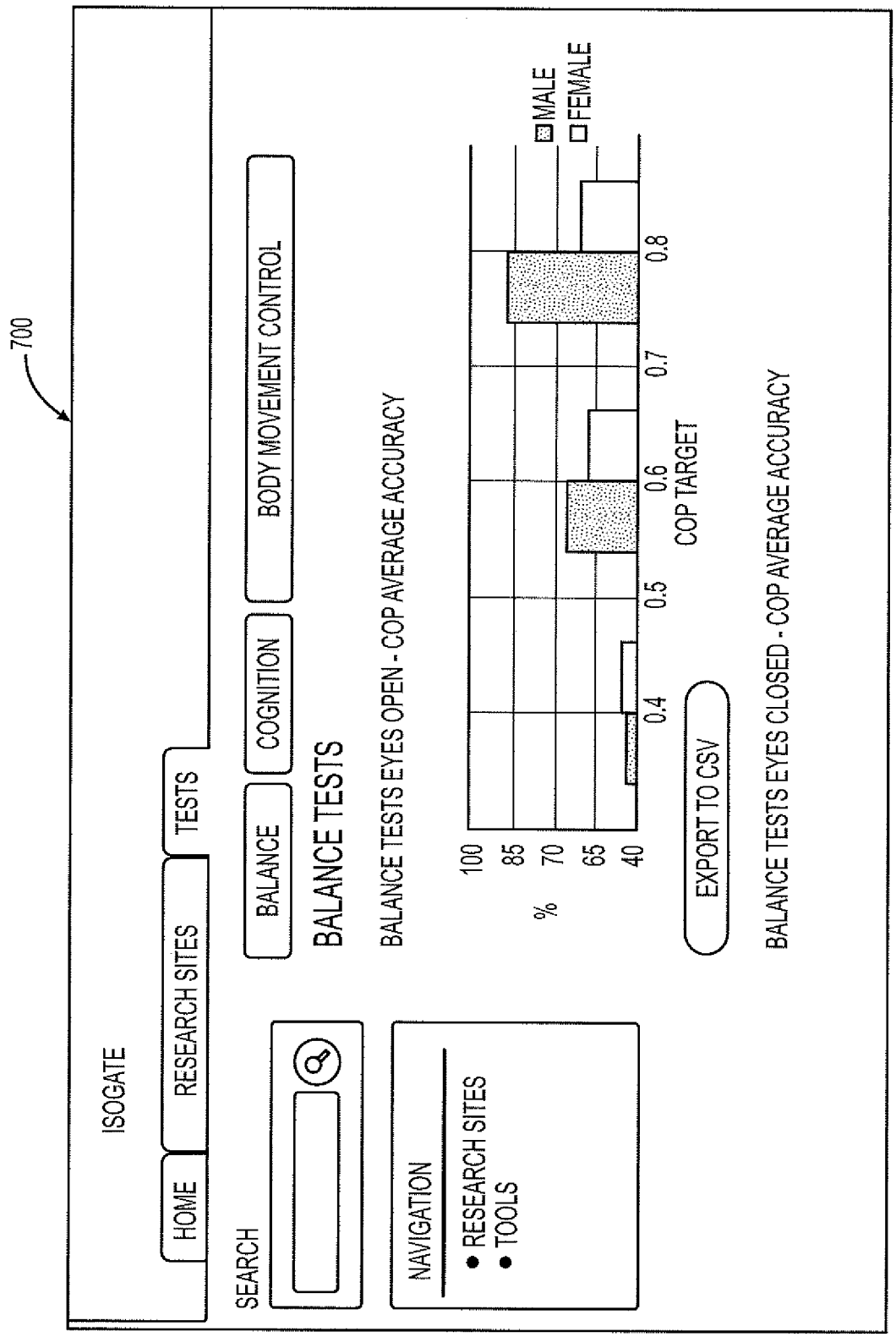
FIG. 19 is a graphic user interface of a research data collection hub in accordance with another embodiment.

FIG. 19 shows a research data portal screen 700, which is configured to provide for storage and retrieval of all data collected from a variety of research systems and databases, for analysis and comparison. All data stored can be de-identified and securely stored using encryption and varying levels of security access.

One purpose of the research data portal is as a research data collection hub for all data from research stations and user sites where data collection equipment is used. Data collection equipment may include balance plate 102 and dynamometer 134. Data can be analyzed, compared and exported using custom filters and drilling down into the data based on groups, ethnicity, gender, age and test types. The research data portal essentially provides a much expanded cumulative research data pool for analysis.

The research data portal can also include a research publications database for researchers to search and download from. The research data portal can also include a member community so members can connect with other members to create collaborative projects and share their experiences using various data collection devices. Additionally, a network template may be built for institutions to store their own data securely and privately. A desktop application and mobile application may be configured that pushes data to the research data portal and allows a user to securely connect to the research data portal.

The foregoing description is by way of example only, and may be varied considerably without departing from the scope of the present invention. For example only, instead of a fixed display to present a test, the system may be modified to utilize virtual reality and/or holographic imagery.

The features described with respect to one embodiment may be applied to other embodiments, or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for patient rehabilitation, the system comprising:
a balance plate for measuring whole of body Center of Pressure (COP) dynamic weight distribution data of a patient, wherein the balance plate comprises a single support surface configured such that the patient stands on the single support surface and at least one load cell configured to detect movement of the patient's COP;
a cognitive assessment module operable to measure the patient's cognitive abilities, wherein the cognitive abilities include short term memory, memory recall, and combinations thereof;
a visual display; and
a processor in operative communication with the balance plate, the processor being configured to generate data pertaining to (a) the ability of the patient to conscientiously move their COP from a first predetermined point to at least a second predetermined point as displayed on the visual display and (b) the patient's cognitive abilities, the data being generated using the COP dynamic weight distribution data measured by the balance plate and the cognitive assessment module.

2. The system of claim 1, wherein the processor is configured to portray the patient's COP as an icon moving across the display in tandem with movement of the patient's COP.

3. The system of claim 1, wherein the processor is configured to cause the display to show the first predetermined point and the second predetermined point.

4. The system of claim 1, wherein movement of the patient's COP from the first predetermined point to the second predetermined point is tracked by the processor and represented as a trace on the display.

5. The system of claim 1, wherein the balance plate is configured to measure an extent of variation of the COP of the patient over a predetermined time period.

6. The system of claim 1, further comprising an electronic database of patient profiles, each profile including at least one record having the data generated by the processor.

7. The system of claim 6, wherein each patient profile includes a plurality of records, the processor being configured to compare more than one of the patient's records in order to permit an evaluation of the patient's rehabilitation.

8. The system of claim 1, wherein the visual display is wearable by the patient.

9. The system of claim 1, further comprising a hand dynamometer configured to accept a patient's grip.

10. The system of claim 9, wherein the hand dynamometer is further configured to measure pressure from the patient's grip over a timed duration.

11. A system for patient rehabilitation, the system comprising:
a balance plate for measuring whole of body Center of Pressure (COP) dynamic weight distribution data of a patient, wherein the balance plate comprises a single support surface configured such that the patient stands on the single support surface and at least one sensor configured to detect movement of the patient's COP;
at least one additional module operable to measure the patient's capacity for planning and foresight through a maze test;
a visual display; and
a processor in operative communication with the balance plate, the processor being configured to generate data pertaining to (a) the ability of the patient to conscientiously move their COP from a first predetermined point to at least a second predetermined point as displayed on the visual display and (b) the patient's capacity for planning and foresight, the data being generated using the COP dynamic weight distribution data measured by the balance plate and test results from the at least one additional module.

12. The system of claim 11, wherein the processor is configured to portray the patient's COP as an icon moving across the display in tandem with movement of the patient's COP.

13. The system of claim 11, wherein the processor is configured to cause the display to show the first predetermined point and the second predetermined point.

14. The system of claim 11, wherein the balance plate is configured to measure an extent of variation of the COP of the patient over a predetermined time period.

15. The system of claim 11, wherein the first predetermined point is a starting position and the second predetermined point is a finishing position, and movement of the patient's COP from the starting position to the finishing position is tracked by the processor and represented as a trace on the display.

16. The system of claim 15, wherein the trace shows the patient's COP movement relative to time.

17. The system of claim 11, further comprising a hand dynamometer configured to measure pressure from a patient's grip.

18. A system for patient rehabilitation, the system comprising:
   a balance plate for measuring a patient's whole of body Center of Pressure (COP) dynamic weight distribution data, the balance plate including a single support surface configured such that the patient stands on the single support surface, and at least one sensor configured to detect movement of the patient's COP;
   at least one additional testing module operable to assess the patient's capacity for planning and foresight;
   a visual display; and
   a processor in operative communication with the balance plate, the processor being configured to generate data pertaining to (a) the ability of the patient to conscientiously move their COP from a first predetermined point to at least a second predetermined point as displayed on the visual display and (b) the patient's capacity for planning and foresight, the data being generated using the COP dynamic weight distribution data measured by the balance plate and the at least one additional testing module,
   wherein movement of the patient's COP from the first predetermined point to the second predetermined point is tracked by the processor and represented as a trace on the display.

19. The system of claim 18, further comprising a hand dynamometer configured to measure pressure from a patient's grip over a timed duration.

20. The system of claim 18, wherein the trace shows the patient's COP movement relative to time.

* * * * *